United States Patent
Mazzillo et al.

(10) Patent No.: US 11,684,273 B2
(45) Date of Patent: Jun. 27, 2023

(54) TUNABLE OPTOELECTRONIC DEVICE AND BLOOD PRESSURE SENSOR INCLUDING THE SAME

(71) Applicant: STMICROELECTRONICS S.R.L., Agrate Brianza (IT)

(72) Inventors: Massimo Cataldo Mazzillo, Corato (IT); Piero Fallica, Catania (IT); Sebania Libertino, Catania (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 1415 days.

(21) Appl. No.: 15/976,658

(22) Filed: May 10, 2018

(65) Prior Publication Data

US 2018/0333060 A1 Nov. 22, 2018

(30) Foreign Application Priority Data

May 17, 2017 (IT) .......................... 102017000053528

(51) Int. Cl.
*A61B 5/021* (2006.01)
*G02F 1/21* (2006.01)
(Continued)

(52) U.S. Cl.
CPC ...... *A61B 5/02125* (2013.01); *A61B 5/02141* (2013.01); *A61B 5/02433* (2013.01);
(Continued)

(58) Field of Classification Search
CPC .... G01J 3/26; G01J 2003/1226; G01J 3/2803; G01J 2001/442; G01J 2001/4466;
(Continued)

(56) References Cited

U.S. PATENT DOCUMENTS

| | | | |
|---|---|---|---|
| 6,230,046 B1 * | 5/2001 | Crane | A61B 5/0059 600/476 |
| 6,381,480 B1 * | 4/2002 | Stoddart | A61B 5/1464 600/338 |

(Continued)

FOREIGN PATENT DOCUMENTS

| | | | | |
|---|---|---|---|---|
| WO | WO-2016174659 A1 * | 11/2016 | ............ | G06F 1/163 |
| WO | 2017/021405 | 2/2017 | | |

OTHER PUBLICATIONS

A. Wong, Kong-Pang Pun, Yuan-Ting Zhang and K. Hung, "A near-infrared heart rate measurement IC with very low cutoff frequency using current steering technique," Dec. 2005, in IEEE Transactions on Circuits and Systems I: Regular Papers, vol. 52, No. 12, pp. 2642-2647, doi: 10.1109/TCSI.2005.857767. (Year: 2005).*

(Continued)

*Primary Examiner* — Jennifer D Bennett
*Assistant Examiner* — Erin R Garber
(74) *Attorney, Agent, or Firm* — Seed IP Law Group LLP

(57) ABSTRACT

In various embodiments, the present disclosure provides devices and systems for detecting the blood pressure of a user. In one embodiment, an optoelectronic device includes an array of avalanche photodiodes operating in Geiger mode. A tunable optical filter is optically coupled to the array and receives a light beam reflected from a vascularized tissue of the user, in response to the vascularized tissue being illuminated by an optical source.

22 Claims, 3 Drawing Sheets

(51) Int. Cl.
*A61B 5/024* (2006.01)
*A61B 5/00* (2006.01)
*G01J 3/26* (2006.01)
G01J 3/12 (2006.01)
G01J 1/44 (2006.01)

(52) U.S. Cl.
CPC .............. *A61B 5/742* (2013.01); *G01J 3/26* (2013.01); *G02F 1/21* (2013.01); *A61B 2562/0238* (2013.01); *G01J 2001/442* (2013.01); *G01J 2001/4466* (2013.01); *G01J 2003/1226* (2013.01); *G02F 1/213* (2021.01); *G02F 2203/055* (2013.01); *G02F 2203/11* (2013.01)

(58) Field of Classification Search
CPC ............ A61B 5/02125; A61B 5/02141; A61B 5/02433; A61B 5/742; A61B 5/029; A61B 5/15003; A61B 2562/0238; G02F 1/21; G02F 1/213; G02F 2203/055; G02F 2203/11
See application file for complete search history.

(56) References Cited

U.S. PATENT DOCUMENTS

| | | | | |
|---|---|---|---|---|
| 9,234,797 | B1* | 1/2016 | Newman | G01J 5/0837 |
| 9,554,738 | B1* | 1/2017 | Gulati | A61B 5/1455 |
| 9,568,418 | B1* | 2/2017 | Hug | G01J 3/36 |
| 2006/0132786 | A1* | 6/2006 | Helbing | G01N 21/77 |
| | | | | 356/446 |
| 2007/0236697 | A1 | 10/2007 | Zribi et al. | |
| 2011/0043823 | A1* | 2/2011 | Hillmer | G01J 3/36 |
| | | | | 356/519 |
| 2014/0323879 | A1* | 10/2014 | Seetamraju | A61B 5/14551 |
| | | | | 600/479 |
| 2014/0333898 | A1* | 11/2014 | Boate | A61B 3/12 |
| | | | | 351/221 |
| 2014/0339398 | A1 | 11/2014 | Mazzillo et al. | |
| 2014/0354996 | A1* | 12/2014 | Fontecchio | G02F 1/13342 |
| | | | | 349/86 |
| 2015/0103343 | A1* | 4/2015 | Smith | G02B 5/201 |
| | | | | 359/578 |
| 2016/0025562 | A1* | 1/2016 | Donlagic | G01J 3/0208 |
| | | | | 250/227.23 |
| 2016/0123809 | A1* | 5/2016 | Learmonth | G01J 3/0208 |
| | | | | 356/454 |
| 2017/0016766 | A1* | 1/2017 | Wijbrans | G01J 3/26 |
| 2017/0089756 | A1* | 3/2017 | Scott | G01S 7/4863 |
| 2017/0118551 | A1* | 4/2017 | Wagner | A61B 5/6898 |
| 2017/0156606 | A1* | 6/2017 | Ferber | A61B 5/6829 |
| 2019/0182415 | A1* | 6/2019 | Sivan | G06F 3/012 |

OTHER PUBLICATIONS

David A. Hampton, Martin A. Schreiber, "Near infrared spectroscopy: clinical and research uses," Jan. 10, 2013, in Transfusion, 53:52S-58S. (Year: 2013).*

P. Buzhan, et al., Silicon photomultiplier and its possible applications, Nuclear Instruments and Methods in Physics Research Section A: Accelerators, Spectrometers, Detectors and Associated Equipment, May 2003, Elsevier, vol. 504, Issues 1-3, pp. 48-52 (Year: 2003).*

Agrò et al., "PPG Embedded Systems for Blood Pressure Monitoring," in *AEIT Annual Conference—From Research to Industry: The Need for a More Effective Technology Transfer (AEIT)*, Trieste, Italy, Sep. 18-19, 2014, 6 pages.

Liu et al., "Multi-wavelength photoplethysmography method for skin arterial pulse extraction," *Biomedical Optics Express* 7(10):4313-4326, 2016.

Oreggia et al., "Physiological parameters measurements in a cardiac cycle via a combo PPG-ECG system," in *AEIT International Annual Conference (AEIT)*, Naples, Italy, Oct. 14-16, 2015, 6 pages.

* cited by examiner

TUNABLE OPTOELECTRONIC DEVICE AND BLOOD PRESSURE SENSOR INCLUDING THE SAME

BACKGROUND

Technical Field

The present disclosure relates to a tunable optoelectronic device and to a blood pressure sensor including the same.

Description of the Related Art

As is known, photoplethysmography is a low-cost optical technology that can be used to detect variations in blood volume within vascularized tissues. This method is currently used in medical devices such as pulse oximeters.

Typically, a system based on plethysmography comprises an LED source, which illuminates a portion of a user's tissue (particularly a portion of skin) with a light beam, and a photodetector, which is placed near the LED source, on the same side of the tissue, and generates a signal which depends on the portion of light beam that is reflected by the tissue; this signal is indicative of the variations of light absorption that take place in the tissue, which in turn depend on the variations of volume of the vascularized tissue caused by blood pulsation. The variations of light intensity detected by the photodetector are therefore indicative of the blood pulsation.

Unfortunately, the use of photoplethysmography for the precise determination of parameters relating to blood flow is particularly difficult. This is because, as is known, sensors based on photoplethysmography have low resolution with respect to the depth of the vascularized tissue.

In greater detail, it is known that, for a vascularized tissue delimited by a portion of skin, capillaries, arterioles and arteries are encountered successively as the depth increases. In other words, a vascularized tissue may be considered as a multi-layer tissue in which each layer has different characteristics as regards the composition of the blood vessels and the capacity for the propagation of blood pulses. Consequently, in the case of an arterial pulse sensor based on photoplethysmography, for example, the LED source is typically of the infrared type, to provide better penetrative capacity of the light beam, making it possible to detect signals originating from the arteries. However, since the light beam always has to pass through portions of tissue closer to the surface, the variations in light intensity detected by the photodetector are a function of the changes in volume affecting all the blood vessels through which the light passes. Because the signal generated by the photodetector depends on a set of blood pulsation signals generated by different types of blood vessels, the accuracy of the subsequent determination of parameters relating to blood flow is reduced.

In order to overcome at least some of the drawbacks described above, solutions have been proposed in which the sensors have a plurality of photodetectors spaced apart, although these generate corresponding signals which originate from different sites, and thus follow paths which are not exactly identical. As an alternative, sensors have been proposed which have optical sources capable of generating optical pulses of very limited duration, together with very fast photodetectors; however, these sensors are extremely costly and difficult to integrate.

Owing to the aforementioned technological problems, photoplethysmography is currently used in the clinical environment solely in pulse oximeters. However, the detection of blood pressure by photoplethysmography is impeded by present-day technological limitations, among which we should mention the presence of artifacts within the signals generated by the photodetectors, due to the noise caused by movements of the user.

The paper by J. Liu et al., "Multi-wavelength photoplethysmography method for skin arterial pulse extraction", Biomedical Optics Express, vol. 7, no. 10, pp. 4313-4326, published 27 Sep. 2016, describes in mathematical terms a method which makes use of the dependence of light penetration on the wavelength to improve the resolution in depth of the determination of blood pulsation signals relating to non-surface portions of vascularized tissue. In particular, this paper suggests the use of two or three light sources having different wavelengths; it also suggests that the vascularized tissue be modeled with a multi-layer structure including two or three vascularized layers. This paper also proposes the modeling of the light-tissue interaction on the basis of a modified Beer-Lambert law and the use of a quasi-analytical calibration algorithm.

In greater detail, the aforementioned paper describes a system including four LED sources, which emit in the infrared, yellow, blue and green respectively, and a photodiode. The system is sampled at 1 kHz, so that four signals are available at the output from the photodiode, these signals being shown in FIG. 1, where they are indicated by PPG1, PPG2, PPG3 and PPG4 respectively.

FIG. 1 also shows an electrocardiogram signal ECG, a signal indicative of the blood pressure (indicated by BP) and a differential signal D-PPG indicative of the arterial pulse, the generation of which signal requires a calibration operation. The time distance between a peak of the signal ECG and a corresponding peak of the differential signal D-PPG represents an estimate D_PTT of what is known as the pulse transit time, which in turn represents the travelling time of a pressure pulse between two different points located along the path followed by an artery. The estimate of the pulse transit time is therefore used as the basis for producing a corresponding estimate of the blood pressure, particularly an estimate of the systolic blood pressure, which is equal to the pressure value of the peaks of the signal BP.

More particularly, the aforementioned paper describes various examples of the differential signal D-PPG, calculated on the basis of models of the vascularized tissue with a single layer, a double layer and a triple layer, resulting in the generation of estimates of the pulse transit time and systolic blood pressure which become more precise with an increase in the number of wavelengths used.

In practice, the aforementioned paper proposes a quasi-analytical mathematical model, which, after calibration, can be used to detect arterial pulses in a more precise way than what was proposed previously, up to the point of allowing the determination, on the basis of the detected pulses, of a physiological quantity of very high clinical importance such as systolic blood pressure.

In view of the above, the estimates of blood pressure that can be produced on the basis of the method described in the aforementioned paper depend on the wavelengths used, as well as on physiological characteristics of the user, such as age, skin color and the position of the sensor, which may, for example, be coupled to a finger or to a wrist. In this context, the aforementioned paper is completely silent on the possibility of providing greater flexibility for the system described therein, which requires variation of the light sources during the search for the optimal wavelengths. Furthermore, the system still suffers from the fact that the optical signals generated by the optical sources do not follow identical optical paths.

BRIEF SUMMARY

In various embodiments, the present disclosure provides an optical blood pressure sensor that can overcome at least some of the drawbacks of the prior art.

In one embodiment, the present disclosure provides an optoelectronic device that includes an array of avalanche photodiodes and a tunable optical filter. The array of avalanche photodiodes are configured to operate in a Geiger mode, and the tunable optical filter is optically coupled to the array and is configured to receive a light beam reflected from a vascularized tissue in response to the vascularized tissue being illuminated by an optical source.

In another embodiment, the present disclosure provides a blood pressure sensor that includes a light source configured to emit a beam of light, and an optoelectronic device. The optoelectronic device includes an array of single photon avalanche diodes (SPADs) and a tunable optical filter optically coupled to the array of SPADs and configured to receive a reflected portion of the light beam that is reflected from a vascularized tissue, and to transmit at least some of the reflected portion of the light beam to the array of SPADs.

In yet another embodiment, the present disclosure provides a blood pressure detection system that includes an optoelectronic sensor, a microcontroller and a processor. The optoelectronic system includes first and second silicon photomultipliers (SiPMs) and a tunable optical filter optically coupled to the first and second SiPMs and configured to receive a reflected portion of a light beam that is reflected from a vascularized tissue, and to transmit at least some of the reflected portion of the light beam to the first and second SiPMs. The first SiPM is configured to detect light within a first range of wavelengths, and the second SiPM is configured to detect light in a second range of wavelengths that is different from the first range. The microcontroller is configured to control the tunable optical filter to transmit respective narrow-band fractions of the reflected portion of the light beam in a plurality of respective time intervals, and the first and second SiPMs are configured to generate, for each of said narrow-band fractions, corresponding electrical signals indicative of the intensity of the narrow-band fraction of the reflected portion of the light beam. The processor is configured to determine an estimate of a blood pressure based on the electrical signals.

BRIEF DESCRIPTION OF THE SEVERAL VIEWS OF THE DRAWINGS

Embodiments of the present disclosure will now be described, purely by way of non-limiting examples, with reference to the attached drawings, in which.

DETAILED DESCRIPTION

Figure 2:
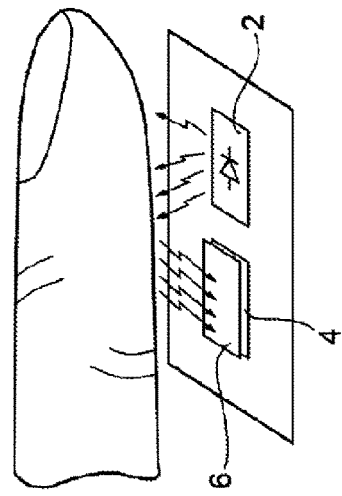
FIG. 2 shows a schematic diagram of a blood pressure sensor, in accordance with one or more embodiments of the present disclosure.

As shown schematically in FIG. 2, the applicant has observed that a highly flexible optical system for blood pressure detection can be produced by coupling a broad-spectrum light source 2, capable of illuminating a vascularized tissue, with a photodetector 4 coupled to a tunable optical filter 6, which receive the radiation emitted by the light source after it has interacted with the vascularized tissue.

Figure 3:
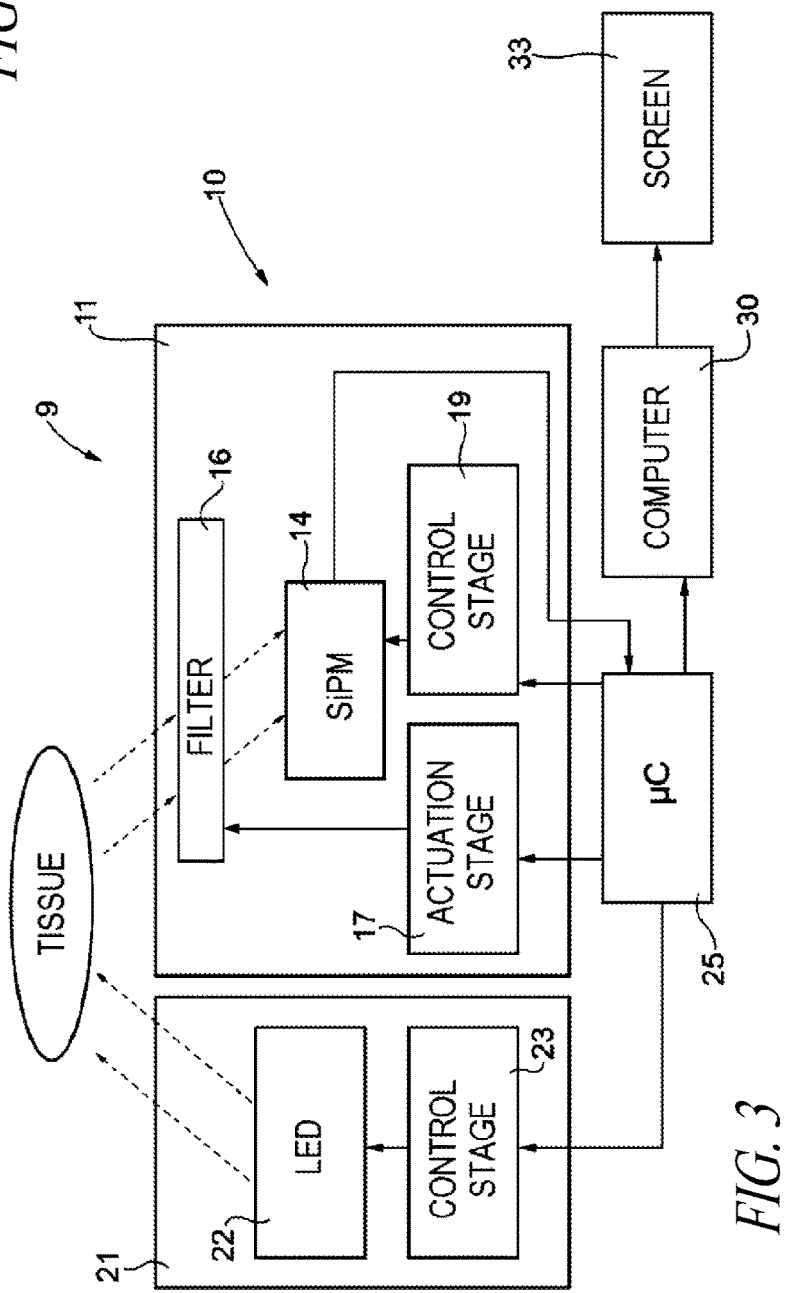
FIG. 3 shows a block diagram of a blood pressure detection system including an optoelectronic device, in accordance with one or more embodiments of the present disclosure.

In greater detail, FIG. 3 shows a detection system 10 which may be optically coupled to a vascularized tissue and acts as a blood pressure sensor, as described below.

The detection system 10 comprises an optoelectronic device 9, which is formed in a first die 11 of semiconductor material (silicon, for example), in which is formed what is known as a silicon photomultiplier (or "SiPM") 14.

The SiPM photomultiplier 14 is formed by an array of avalanche photodiodes operating in Geiger mode ("Geiger-mode avalanche photodiodes", or GM-APD), also known as single photon avalanche diodes (or "SPAD"). Each SPAD photodiode forms a junction of semiconductor material which is biased, in use, with a reverse bias voltage which is higher, in modulus, than the breakdown voltage of the junction, so that the generation of a single electron-hole pair, due to the absorption of a photon within the photodiode SPAD, may be sufficient to initiate a high-gain avalanche ionization process, resulting in the generation of what is known as an avalanche current in a short time (e.g., measured in hundreds of picoseconds).

A Fabry-Perot interference filter 16 is also formed in the first die 11. An actuation stage 17 and a first control stage 19, described below, are also formed in the first die 11.

The detection system 10 further comprises a second die 21, in which an LED 22 and a second control stage 23 are formed. Without any loss of generality, the first and second dies 11, 21 are positioned, in use, on the same side of the vascularized tissue.

In detail, the LED 22 is capable of emitting broad-spectrum light, such as visible white light, that is to say radiation formed by a plurality of components have wavelengths in the range from 400 nm to 700 nm, or possibly from 400 nm to 1000 nm. The LED 22 is also biased by the second control stage 23. The light emitted by the LED 22 is referred to below as the first light beam. Without any loss of generality, the LED 22 may have an emission angle in the range from 60° to 120°.

When the vascularized tissue is coupled to the detection system 10 for operation, the first light beam strikes the tissue. The interaction between the first light beam and the vascularized tissue includes the generation of a second light beam, which is directed towards the detection system 10 and is formed by the radiation reflected and the radiation back-scattered by the vascularized tissue.

The interference filter 16 is controlled by the actuation stage 17. For example, the interference filter 16 may form a cavity (not shown) which is at least partially delimited by a piezoelectric element (not shown), which is electrically coupled to the actuation stage 17. The actuation stage 17 therefore electrically controls the optical length of the cavity, by acting electrically on the piezoelectric element; thus the actuation stage 17 controls the interference filter 16, and particularly the corresponding pass bands and attenuated bands. For example, the pass band of the interference filter 16 may be tuned with steps of 30 nm in the emission band of the LED 22; the pass band of the interference filter 16 may also have a full width half maximum (FWHM) in the range from 20 to 30 nm; additionally, the interference filter 16 may have a band center wavelength switching time in the range from 50 to 100 μs. In some embodiments, the Fabry-Perot interference filter 16 may have a switching time in a range from 1 μs to 100 μs.

As regards the SiPM photomultiplier 14, the SPAD photodiodes may be biased, in a known way, at the same reverse bias voltage; additionally, the avalanche currents generated within the SPAD photodiodes are multiplied together so as to generate an output signal of the SiPM photomultiplier 14 equal to the sum of the avalanche currents generated within the SPAD photodiodes. The SiPM photomultiplier 14 is therefore a device with a broad area and high gain, capable of supplying, on the average, an output (current) signal proportional to the number of photons striking the SiPM photomultiplier 14.

More particularly, with reference to the third light beam to indicate the fraction of the second light beam that strikes the interference filter 16 and is transmitted by the latter, the output signal generated by the SiPM photomultiplier 14 is directly proportional to the intensity of the third light beam.

In greater detail, the first control stage 19 is capable of biasing the SPAD photodiodes of the SiPM photomultiplier 14, the output of which may be connected to a microcontroller unit 25 of the detection system 10, as shown in FIG. 3.

In turn, the microcontroller unit 25 may control the first and second control stage 19, 23, together with the actuation stage 17. The microcontroller unit 25 may also transmit a signal, referred to below as the preconditioned signal, to a computer 30. The preconditioned signal is generated by the microcontroller unit 25 on the basis of the output signal generated by the SiPM photomultiplier 14 and is also indicative of the intensity of the third light beam.

In even greater detail, the SiPM photomultiplier 14 has a particularly short detection time. In this context, in order to prevent the avalanche events initiated in the SPAD photodiodes from becoming self-sustaining, thus obstructing the detection of subsequent photons, the SPAD photodiodes are coupled to corresponding quenching resistors, also formed in the SiPM photomultiplier 14. The quenching resistors enable the ionization processes to be inhibited for a time known as the hold-off time, so as to reduce the effective voltages across the junctions of the SPAD photodiodes and thus avalanche currents, before the first control stage 19 restores the initial bias conditions. Consequently, the recovery time of the SiPM photomultiplier 14 is equal to approximately 1 μs, so that the output signal cannot be sampled at frequencies greater than 1 MHz. In some embodiments, the recovery time of the SiPM photomultiplier 14 is less than 1 μs, and is in a range from about one hundred nanoseconds to about 1 μs. While Fabry Perot filters generally allow switching times of about 50 μs, other solutions are being studied which may lower the switching time to as low as a few microseconds, or even lower. SPAD or SiPM photomultipliers may be the only currently available solid state detectors that are able to follow in free-running mode (that is, without switch-off electronics) these fast switching times, which may ideally be characterized by rising times lower than 1 ns and recovery times of hundreds of nanoseconds. Accordingly, SiPM photomultipliers facilitate significantly lowering the analysis time or increasing in the same analysis time the number of wavelengths detected, which may increase the accuracy of the analysis.

Regarding the microcontroller unit 25, on the other hand, this may include a corresponding analog-to-digital converter (not shown) capable of sampling the output signal generated by the photomultiplier 14, in order to generate the preconditioned signal.

In use, the microcontroller unit 25 may control the actuation stage 17 so as to vary the pass band of the interference filter 16, in such a way that the third light beam is monochromatic to a first approximation, at a desired wavelength.

In practice, assuming for example that there are a first, a second and a third time interval not overlapping one another, the third light beam may have a wavelength of $\lambda_{11}$, $\lambda_{21}$, and $\lambda_{31}$ respectively. Consequently, the output signal generated by the SiPM photomultiplier 14 during the first, second and third time interval are referred to below as the first, second and third detection signal, respectively; additionally, the first, second and third preconditioned signal are referred to below to indicate the signals generated by the microcontroller unit 25 on the basis of the first, second and third detection signal, respectively.

The computer 30 then processes at least two of the first, second and third preconditioned signals, or all three of the preconditioned signals, for example, on the basis of the method described in the aforementioned paper by J. Liu et al., "Multi-wavelength photoplethysmography method for skin arterial pulse extraction" which is incorporated by reference herein in its entirety, to determine a quantity indicative of the arterial pulse of a non-surface (internal) layer of the vascularized tissue. The computer 30 then determines a further pair of quantities, which are indicative, respectively, of the pulse transit time and the systolic blood pressure. The computer 30 may be or otherwise include a computer processor, which may be programmed to perform the various operations described herein with respect to the computer 30, including, for example, determining an estimate of blood pressure based on the preconditioned signals.

Also with reference to the processes executed by the computer 30 and to the aforementioned further pair of quantities, without any loss of generality it is assumed that the user's pressure remains substantially constant during the first, second and third time interval, each of which may have a duration of 10 μs, for example. In this context, the first, second and third detection signal may be sampled, for example, at a frequency of 1 kHz.

The microcontroller unit 25 may also iterate the operations described above. In other words, on each iteration, microcontroller unit 25 controls the actuation stage 17 in such a way that, in three corresponding time intervals, the third light beam has a wavelength of $\lambda_{1n}$, $\lambda_{2n}$, $\lambda_{3n}$ respectively. On each iteration, the microcontroller unit 25 therefore generates corresponding preconditioned signals, on the basis of which the computer 30 determines corresponding quantities indicative of the arterial pulse of the aforementioned non-surface layer of the vascularized tissue, the pulse transit time, and the blood pressure.

The values of blood pressure determined by the computer 30 may be displayed on a display or screen 33 which is coupled to the computer 30. Additionally, by comparison with the pressure value detected by a conventional instrument (such as a sphygmomanometer), it is possible to select the pair or triplet of wavelengths that provide more precise estimates of the blood pressure for a given patient and a given coupling between the patient and a detection system 10.

The advantages provided by the present optoelectronic device are clearly apparent from the above description. In particular, if a photomultiplier is coupled to a tunable optical filter capable of selecting quasi-monochromatic components of a broad-spectrum radiation, a high degree of flexibility and rapidity are achieved in the selection of the number and values of optimal wavelengths for measuring the blood pressure by photoplethysmography. It is therefore possible to use any number of wavelengths, including a number exceeding three; for this purpose, the operator adjusts a tunable optical filter.

The use of the photomultiplier also allows better discrimination between the AC components of the arterial blood pulsation, important for the determination of the pressure, and the DC components relating to the venous flow which are irrelevant for the determination of the pressure, because of the high gain and low noise.

Finally, the present optoelectronic device can evidently be modified and varied without departure from the scope of the present disclosure.

For example, the first control stage 19 and/or the actuation stage 17 may be formed in a die other than the first die 11, or in different dies from one another. Similarly, the second control stage 23 may be formed in a die other than the LED 22. It is also possible for the interference filter 16 to be formed outside the first die 11, in which case it is mechanically uncoupled from the SiPM photomultiplier 14.

The SiPM photomultiplier 14 may be formed of a semiconductor material other than silicon. More generally, the first and second dies 11, 21 may be formed of semiconductor materials other than those described. Additionally, the LED 22 may be replaced by a broad-band optical source of a type other than that described. In general, in order to limit possible differences between the optical paths followed by optical components having different wavelengths, it is possible to use any white source having an emission area of not more than 1 mm², which emits in a symmetrical manner with an angle in the range from 60° to 120°.

Also with reference to the optical source, since the emission of this source may not be perfectly uniform in the wavelengths concerned, the microcontroller unit 25 of the computer 30 may perform compensation/calibration operations for cancelling the differences between the intensities at which components at different wavelengths are emitted.

The detection system 10 may also include an amplifier for amplifying the output signal generated by the SiPM photomultiplier 14.

Figure 4:
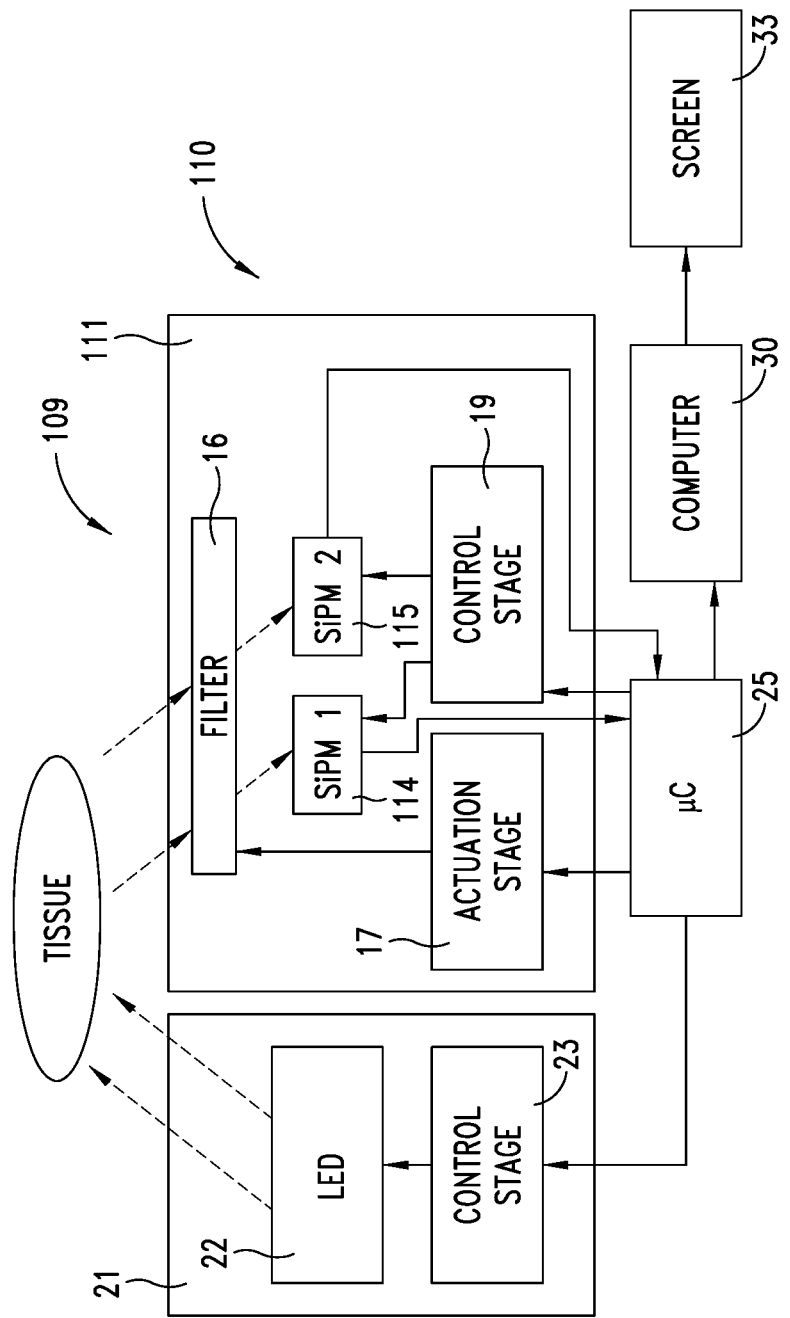
FIG. 4 shows a block diagram of another blood pressure detection system including an optoelectronic device, in accordance with one or more embodiments of the present disclosure.

It is also possible for the detection system 10 to comprise a plurality of SiPM photomultipliers, possibly optimized for different wavelengths, as shown in FIG. 4.

Figure 1:
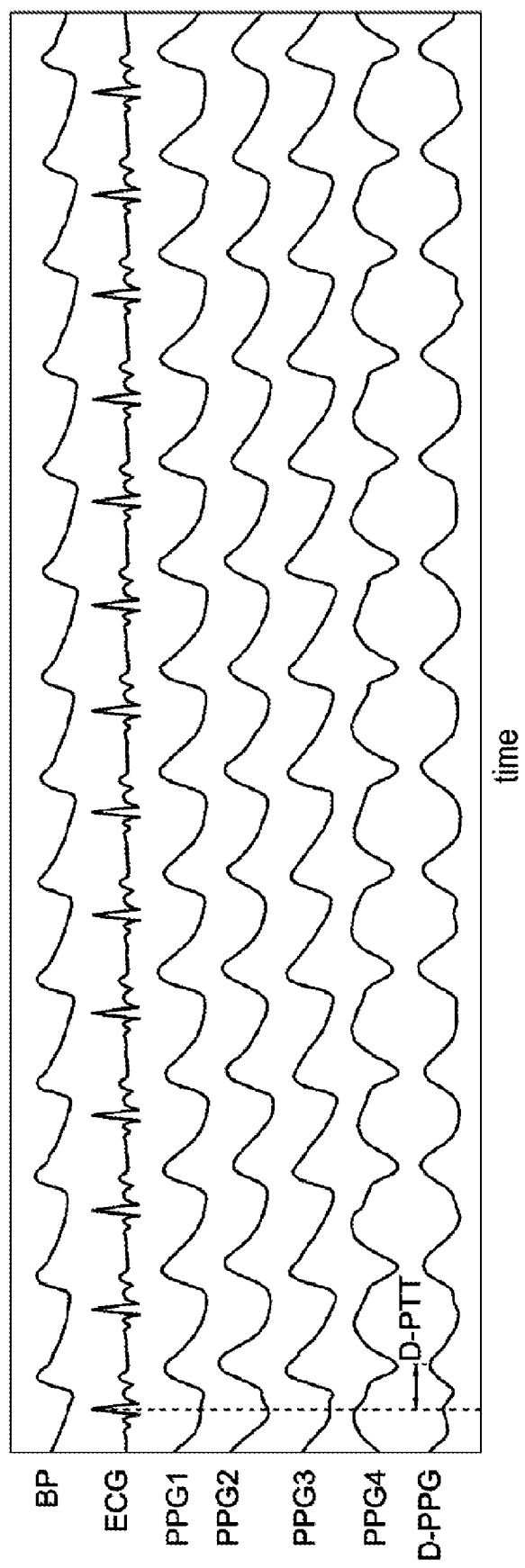
FIG. 1 shows variations with time of signals generated in an optical blood pressure sensor of a known type.

FIG. 4 shows a block diagram of another blood pressure detection system 110 including an optoelectronic device 109, in accordance with one or more embodiments of the present disclosure. The blood pressure detection system 110 of FIG. 4 is substantially the same as the blood pressure detection system 10 shown in FIG. 1, except for the differences that will be discussed below. The main difference is that the optoelectronic device 109 of the blood pressure detection system 110 includes two separate SiPM photomultipliers, which are configured to detect different ranges of wavelengths of light. A first SiPM photomultiplier 114 may be a P/N type SiPM photomultiplier having a layer of p-type material on a layer of n-type material. A second SiPM photomultiplier 115 may be a N/P type, with a layer of n-type material on a layer of p-type material. The first SiPM photomultiplier 114 is more sensitive to shorter wavelength photons (e.g., blue and green), while the second SiPM photomultiplier 115 is more sensitive to longer wavelength photons (e.g., green to near infrared). The first and second SiPM photomultipliers 114, 115 may be formed on a same second die 111, which is substantially the same as the second die 11 shown in FIG. 3, except that the second die 111 includes two separate SiPM photomultipliers instead of one.

The first SiPM photomultiplier 114 may be configured for detection of radiation having wavelengths below about 500 nm, and the second SiPM photomultiplier 115 may be configured for detection of radiation having wavelengths between about 500 nm and about 1000 nm. By including two SiPM photomultipliers, e.g., a first SiPM photomultiplier 114 of P/N type and a second SiPM photomultiplier 115 of N/P type, the detection system 110 is capable of reading with high detection efficiency, high switching speed, and high gain (which is desirable to have a consistent AC/DC ratio) a large number of wavelengths in a wide spectral range (e.g., in a range of about 400-1000 nm), which may advantageously be employed by the multi-wavelength analysis described herein with respect to various implementations for the measurement of blood pressure.

In addition, the use of SiPM photomultipliers significantly reduces the power required for the operation of the LED 22 as compared to standard detectors. For example, using one or more SiPM photomultipliers may reduce the power for operating the LED 22 from about 100 mW in an implementation using standard detectors to about 10 mW in implementations using one or more SPAD or SiPM photomultipliers as detectors. This is due to the intrinsic high amplification of the photodiode which allows for a significant reduction in the light output emitted by the source, and therefore similarly allows for a significant reduction in the operating voltage of the light source.

Finally, although the detection systems 10, 110 have been described with reference to a optical system of the reflection type, it is possible to use forms of detection implementing an optical system of the transmission type, that is to say forms of detection in which the optical source is placed on the opposite side of the vascularized tissue from the side on which the interference filter 16 and the SiPM photodetector 14 are placed.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An optoelectronic device, comprising:
 a first array of avalanche photodiodes configured to operate in a Geiger mode and detect light within a first range of wavelengths;
 a first silicon photomultiplier (SiPM) having a P/N type and including the first array;
 a second array of avalanche photodiodes configured to operate in the Geiger mode and detect light within a second range of wavelengths that is different from the first range of wavelengths;
 a second SiPM having a N/P type and including the second array;
 a tunable optical filter optically coupled to the first array and the second array, the tunable optical filter configured to receive a light beam reflected from a vascularized tissue in response to the vascularized tissue being illuminated by an optical source, and to transmit the light beam reflected from the vascularized tissue to the first array and the second array; and a processor coupled to the first array, the second array, and the tunable optical filter, the processor configured to determine an estimate of a blood pressure based on the light beam reflected from the vascularized tissue.

2. The optoelectronic device according to claim 1 wherein the tunable optical filter is a Fabry-Perot cavity.

3. The optoelectronic device according to claim 2, further comprising an actuation stage configured to electrically control an optical length of the Fabry-Perot cavity.

4. The optoelectronic device according to claim 2 wherein the tunable optical filter has a switching time in a range from 1 μs to 100 μs.

5. The optoelectronic device according to claim 1, further comprising a die, the first array and the tunable optical filter being formed in the die.

6. The optoelectronic device according to claim 1, further comprising an actuation stage configured to control a pass band of the tunable optical filter.

7. The optoelectronic device according to claim 1 wherein the first range of wavelengths is below 500 nm, and the second range of wavelengths is between 500 nm and 1000 nm.

8. A blood pressure sensor, comprising:
a light source configured to emit a light beam; and
an optoelectronic device, including:
an array of single photon avalanche diodes (SPADs);
a tunable optical filter optically coupled to the array of SPADs, the tunable optical filter being a Fabry-Perot interference filter having a cavity, the tunable optical filter configured to receive a reflected portion of the light beam that is reflected from a vascularized tissue;
an actuation stage coupled to the tunable optical filter, the actuation stage configured to vary a pass band of the tunable optical filter by varying an optical length of the cavity, the actuation stage configured to vary the pass band of the tunable optical filter to transmit, in a first time interval, a first detection signal of the reflected portion of the light beam to the array of SPADs, and to transmit, in a second time interval, a second detection signal of the reflected portion of the light beam to the array of SPADs, the first detection signal having a first wavelength, the second detection signal having a second wavelength different from the first wavelength; and
a processor coupled to the array of SPADs, the tunable optical filter, and the actuation stage, the processor configured to determine an estimate of a blood pressure based on the first detection signal and the second detection signal.

9. The blood pressure sensor according to claim 8 wherein said light source has an emission area equal to or less than 1 mm$^2$.

10. The blood pressure sensor according to claim 8, wherein said light source has an emission angle in a range from 60° to 120°, inclusive.

11. The blood pressure sensor according to claim 8 wherein said light source is configured to emit an initial broad-band light beam towards the vascularized tissue, and wherein the tunable optical filter is electronically controllable to select a number of narrow-band fractions of the light beam.

12. The blood pressure sensor according to claim 11 wherein said number of narrow-band fractions is greater than or equal to three.

13. The blood pressure sensor according to claim 11, further comprising a microcontroller configured to control the tunable optical filter in such a way that, in a plurality of time intervals, the array of SPADs receives a corresponding plurality of narrow-band optical signals formed by corresponding narrow-band fractions of the reflected portion of the light beam, said array of SPADs being configured to generate, for each of said narrow-band optical signals, a corresponding electrical signal indicative of an intensity of the narrow-band optical signal.

14. The blood pressure sensor according to claim 8 wherein the optoelectronic device further includes:
a controller coupled to the array of SPADs and configured to supply a reverse biasing voltage to each of the SPADs of the array of SPADs.

15. The blood pressure sensor according to claim 8 wherein the light source is formed in a first die, and the optoelectronic device is formed in a second die that is separate from the first die.

16. The blood pressure sensor according to claim 8 wherein the light source is a light emitting diode (LED) configured to emit the light beam having wavelengths in a range from 400 nm to 1000 nm, inclusive.

17. A blood pressure detection system, comprising:
an optoelectronic sensor, including:
a first silicon photomultiplier (SiPM) having a P/N type and configured to detect light within a first range of wavelengths;
a second SiPM having a N/P type and configured to detect light within a second range of wavelengths, the second range being different from the first range; and
a tunable optical filter optically coupled to the first and second SiPMs and configured to receive a reflected portion of a light beam that is reflected from a vascularized tissue, and to transmit at least some of the reflected portion of the light beam to the first and second SiPMs;
a microcontroller configured to control the tunable optical filter to transmit respective narrow-band fractions of the reflected portion of the light beam in a plurality of respective time intervals, the first and second SiPMs being configured to generate, for each of said narrow-band fractions, corresponding electrical signals indicative of an intensity of the narrow-band fraction of the reflected portion of the light beam; and
a processor configured to determine an estimate of a blood pressure based on the electrical signals.

18. The blood pressure detection system according to claim 17, further comprising:
a light source configured to emit the light beam toward the vascularized tissue.

19. The blood pressure detection system according to claim 18 wherein the light source is formed in a first die, and the optoelectronic sensor is formed in a second die that is separate from the first die.

20. The blood pressure detection system according to claim 18 wherein the light source is a light emitting diode (LED) configured to emit the light beam having wavelengths in a range from 400 nm to 1000 nm, inclusive.

21. The blood pressure detection system according to claim 20 wherein, in operation, a power consumption of the light source is equal to or less than 10 mW.

22. The blood pressure detection system according to claim 17, further comprising:
a display device coupled to the processor, the display device configured to display values associated with the determined estimate of the blood pressure.

* * * * *